United States Patent [19]
Alpern et al.

[11] Patent Number: 5,160,262
[45] Date of Patent: Nov. 3, 1992

[54] DENTAL ARTICULATOR

[75] Inventors: Michael C. Alpern, Charlotte; Ralph J. Brandon, Punta Gorda; Douglas G. Nuelle, Port Charlotte, all of Fla.

[73] Assignee: Ormco Corporation, Glendora, Calif.

[21] Appl. No.: 650,874

[22] Filed: Feb. 5, 1991

[51] Int. Cl.$^5$ .............................................. A61C 11/00
[52] U.S. Cl. ...................................... 433/58; 433/57; 433/59; 433/64
[58] Field of Search .................... 433/55, 57, 58, 59, 433/61, 62, 63, 64, 65, 56

[56] References Cited

U.S. PATENT DOCUMENTS

| | | | |
|---|---|---|---|
| D. 261,805 | 11/1981 | Edwardson | D24/10 |
| 1,022,055 | 4/1912 | Weiss | 433/64 |
| 1,670,311 | 5/1928 | Musante | 433/55 |
| 1,989,367 | 1/1935 | Keeney | 433/58 |
| 2,617,195 | 11/1952 | Perkell et al. | 433/65 |
| 3,159,915 | 11/1962 | Beu et al. | 433/57 |
| 3,423,834 | 1/1969 | Irish | 433/59 |
| 3,908,271 | 9/1975 | Derda et al. | 433/58 |
| 4,047,302 | 9/1977 | Cheythey | 433/56 |
| 4,245,987 | 1/1981 | Bertoldi | 433/61 |
| 4,290,754 | 9/1981 | Edwardson | 433/56 |
| 4,439,150 | 3/1984 | Edwardson | 433/56 |
| 4,453,918 | 6/1984 | Edwardson | 433/55 |
| 4,496,319 | 1/1985 | Steinbeck | 433/57 |
| 4,496,320 | 1/1985 | Hwang et al. | 433/60 |
| 4,505,674 | 3/1985 | Edwardson | 433/59 |
| 4,541,807 | 9/1985 | Rolfs | 434/264 |
| 4,695,252 | 9/1987 | Edwardson | 433/73 |

Primary Examiner—John J. Wilson
Attorney, Agent, or Firm—Wood, Herron & Evans

[57] ABSTRACT

A dental articulator having a upper support member for supporting a dental cast and a lower support member for supporting a second dental cast. A polycentric hinge joint is provided for simulating the temporomandibular joint of a patient. The polycentric hinge joint comprises a fossae block secured to the upper support member and a condyle member secured to the lower support member which engages a fossae recess in the fossae block. A spring is provided for securing the lower support member to the upper support member and simulating the muscles used for mastication. A pair of wires are provided for simulating the ligaments of a patient. The upper end of each wire passes through an opening in the upper support member. The lower end of each wire is secured to the lower support member. A limiting block is provided on the upper end of each of the wires so as to restrict its movement. Removable adjustment rods are provided at the forward end and rear end of the articulator so that the upper and lower support members may be spaced apart a desired distance.

27 Claims, 9 Drawing Sheets

DENTAL ARTICULATOR

The present invention relates to dental articulators for use in making dental casts or orthodontic models and for the correction of occlusion of natural dentition. A dental articulator according to the present invention is designed to produce accurate replication of the various movements of the patient's lower jaw with respect to the temporomandibular joint, thus allowing for the replication of the patient's teeth and the effect on the temporomandibular joint under various conditions.

BACKGROUND OF THE INVENTION

Typical prior art dental articulators comprise an upper principal member and a lower principal member which simulate the temporomandibular condylar joint through the use of balls, associated with either the upper or lower principal member, which are received in a slot in the opposing principal member. However, these articulators involve certain compromises from the standpoint of actual kinetics of the relative movements of the mandible relative to the maxilla. Due to the ball and slot arrangement of prior art articulators, the devices are unable to take into consideration the actual configurations of the temporomandibular joint of the patient. Additionally, prior art articulators do not take into account the forces provided by the ligaments and/or muscles of the jaw. Prior art articulators also fail to take into account the actual movement of the lower jaw as the teeth on the maxilla are moved which is in contrast to the actual movement of the mandible of the patient.

Applicants have invented a novel and improved articulator which closely replicates actual human jaw movement and takes into consideration the actual forces applied by the muscles and ligaments in the jaw. Additionally, an articulator made in accordance with the present invention has the ability to take into account variations in the actual configuration of the condyle and fossae of the patient. The present invention also provides means for allowing easy viewing of the lower dental prosthetic and manipulation of the lower jaw member.

SUMMARY OF THE INVENTION

In one aspect of the present invention there is provided a dental articulator having an upper support members for supporting a first dental cast and a lower support member for supporting a second dental cast. A polycentric hinge joint is provided for simulating the temporomandibular condylar joint and for securing the lower support member to the upper support member. The polycentric hinge joint comprises a pair of axially spaced fossae block secured to the upper support members. Each block has a fossae recess designed to receive a condyle secured to the lower support member. Means are provided for securing the lower support member to the upper support member and for simulating the muscles used for mastication.

In another aspect of the present invention there is provided a dental articulator having an upper support member for supporting a first dental cast and a lower support member for supporting a second dental cast. Joint means are provided for receiving the lower support member to said upper support member and for simulating the temporomandibular condylar joint. Means are provided for positioning the lower support member with respect to the upper support member at a desired position which comprises a first removable adjustment rod located at the forward end of the articulator and at least one removable rear adjustment rod located at the rear end of the articulator. Means are provided for the positioning and locking of the first removable adjustment rod and at least one rear adjustment end at the desired position.

In yet another aspect of the present invention there is provided a dental articulator having an upper support member for supporting a first dental cast and a lower support member for supporting a second dental cast. Joint means are provided for securing the lower support member to the upper support member and for simulating the temporomandibular condylar joint. The articulator further included a neck portion secured at the rear end of the upper support member and a base portion secured at the lower end of the neck portion. Means are also provided so that the neck portion can be readily disconnected from said base portion.

DETAILED DESCRIPTION OF THE INVENTION

Figure 1:
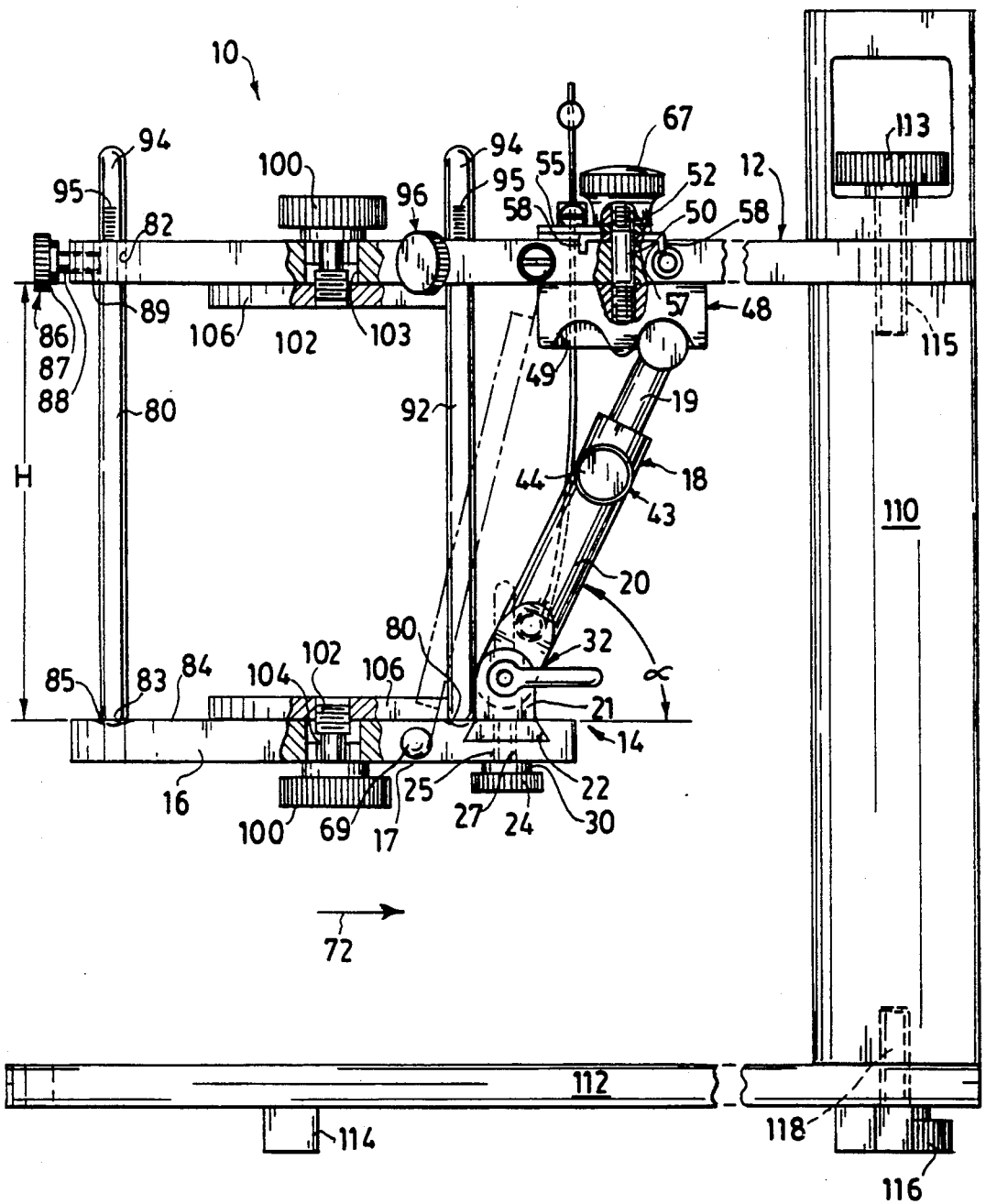
FIG. 1 is a side elevational view of an articulator made in accordance with the present invention.
Figure 2:
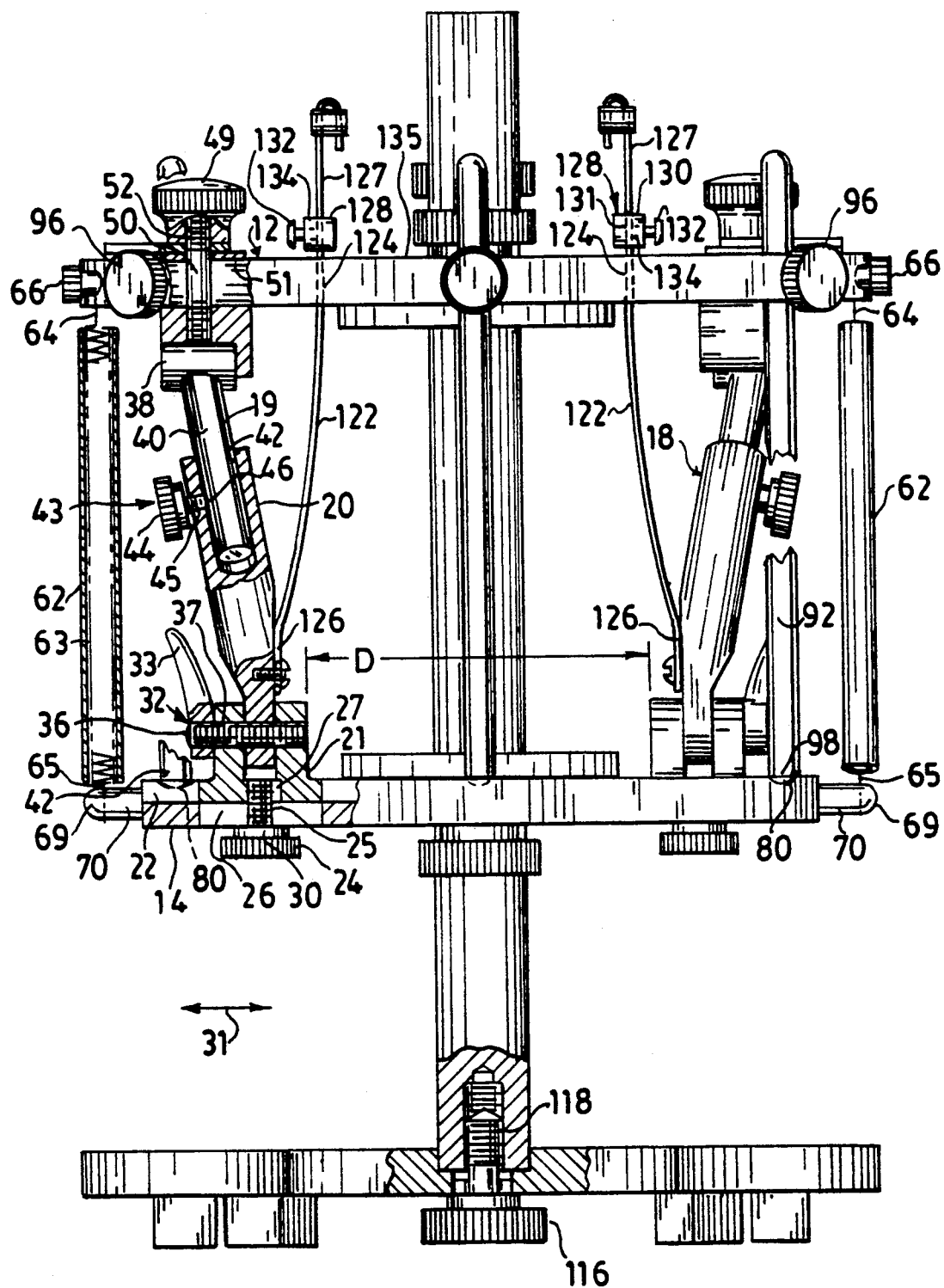
FIG. 2 is a front elevational view, partially broken away, of the articulator of FIG. 1.
Figure 3:
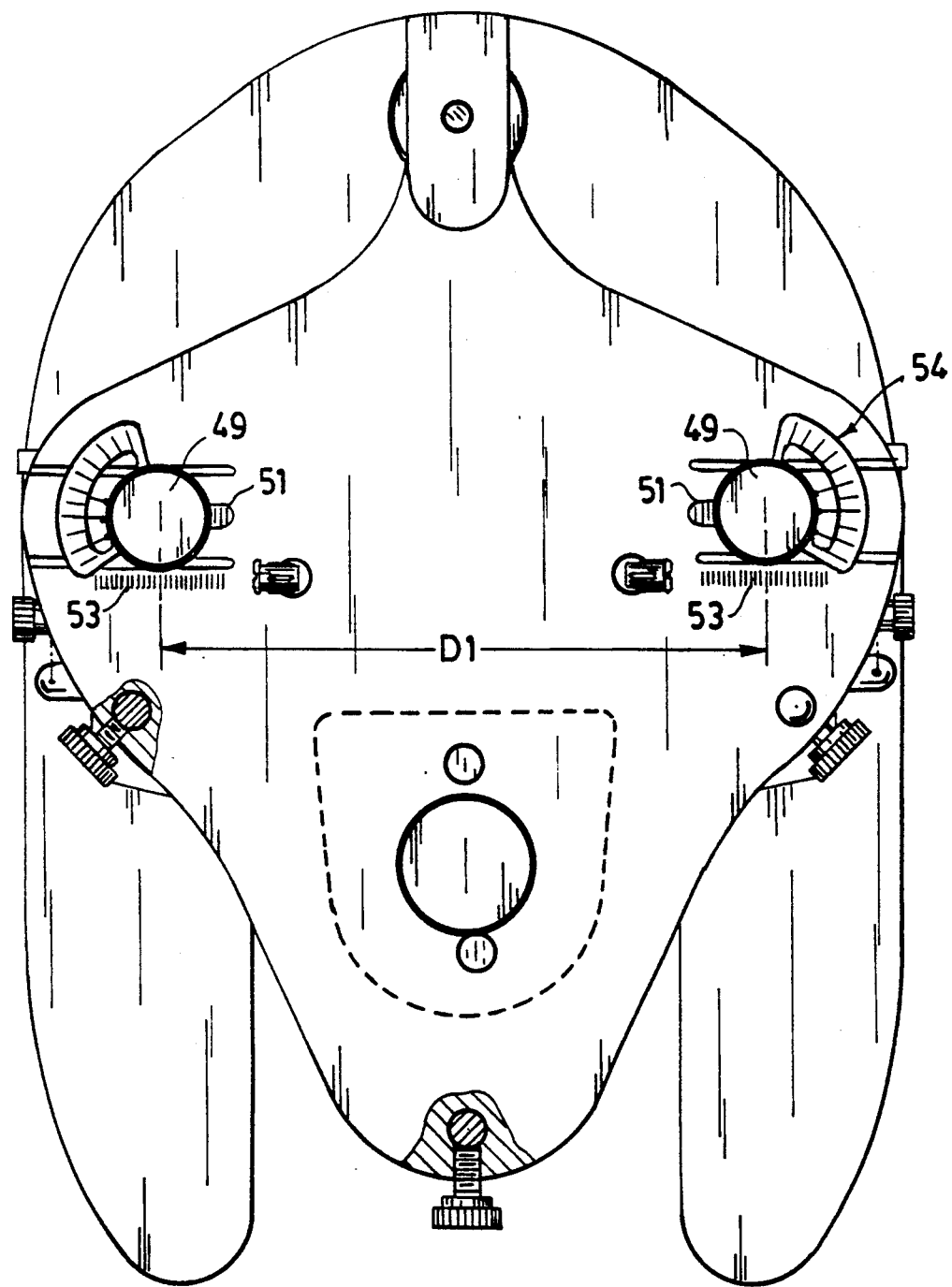
FIG. 3 is a top plan view of the articulator of FIG. 2.

Referring to FIGS. 1-4 there is illustrated a dental articulator 10 made in accordance with the present invention which is typically used for the supporting of dental casts or orthodontic models. The articulator 10 includes an upper support member 12 supporting a first dental cast 13 and a lower support member 14 supporting a second dental cast 15. The lower support member 14 comprises a base member 16 which supports the second dental cast 15 and a pair of axially spaced condyle support members 18. In the particular embodiment illustrated, each condyle support member 18 includes a condyle 19, a central support section 20 and lower mounting end 21. The lower mounting end 21 of each condyle support member is slidably mounted to base member 16. In the embodiment illustrated, lower mounting end 21 is designed to slide within an axial extending slot 22 in base member 16. Associated with each lower mounting end 21 is a hand tightening means for securing mounting member 21 to base member 16 which includes a knob 24 having a threaded shaft 25 designed to pass through an axial extending slot 26 in base member 16 and engage a threaded opening 27 in lower end 21. As knob 24 is turned so that the threads of shaft 25 engage the threads of opening 27, the shank 30 of shaft 25 will press against the lower surface 17 of base member 16 so as to lock lower mounting end 21 in position. To move lower mounting end 21, knob 24 is simply rotated in the opposite direction so that lower mounting end 21 can slide in slot 22. As illustrated in FIG. 1, slot 22 has a dovetail cross sectional shape designed to receive a corresponding mating configuration in the lower mounting end 21 of condyle support member 18 so as to prevent vertical movement therebetween. Therefore, the condyle support member 18 may freely slide in the axial direction indicated by arrows 31, thus, allowing the two condyle support members to be spaced axially apart a distance D as desired by the user.

Preferably, as illustrated, means are provided for adjusting the angle of condyle support member 18 with respect to the base member 16. In the particular embodiment illustrated, this is accomplished by a locking joint 32 which rotatably connects central support section 20 to lower mounting end 21. Locking joint 32 includes a lever 33 having a shaft 36 which passes through aligned opening 37,39 in lower mounting end 21 and central support section 20. When lever 33 is rotated 90° it will either lock or unlock the central support section 20 and lower end so as to allow orientation of the base member 16 to any desired angle α. It is, of course, understood that means for adjusting the angle of orientation of condyle support member 18 may be varied as desired, the illustrated locking joint being but one example. Further, if so desired, the condyle support member 18 need not be provided with any adjustable means, if so desired.

Each condyle 19 is slidably mounted to its associate central support section 20. Referring to FIGS. 1, 2, 8A and 8B, each condyle 19 comprising of an upper engaging section 38 and mounting section 40 extending therefrom. In this embodiment illustrated mounting section 40 comprises of a cylindrical shaft which is designed to slide within an opening 42 in the central support section 18. Mounting section 40 is adjustable positioned within opening 42 by locking means 43. Locking means 43 comprises a knob 44 which has a threaded shaft 45 secured thereto which engages a threaded opening 46 in central support section 20 which communicates with opening 42. By turning knob 44 in the opposite direction, the threaded shaft 45 will bear against mounting section 40 so as to secure condyle 19 in the desired position. By turning knob 44 in the opposite direction, condyle 19 will be released allowing repositioning or removal from central support section 20. Upper engaging section 38 has an outer engaging surface 47 designed to engage a fossae recess 41 in its associated fossae block member 48 which is secured to upper support member 12. A forward capture recess 49 is provided in fossae block member 48 to capture and receive engaging section 38 in the event that engaging section 38 comes out of its associated fossae recess 41. The area between the fossae recess 41 and capture recess 49 simulating the superior eminence of the temporomandibular joint. The fossae block members 48 are each slidably mounted with respect to upper support member 12 such that the axial distance D1 therebetween may be varied as desired. In the particular embodiment illustrated, each fossae block member 48 is axially adjustable through the use of knob 49. A threaded shaft member 50 is secured to fossae block member 48 and passes through a respective axial extending slot 51 formed in upper support member 12. The threaded shaft member 50 is designed to engage a threaded opening 52 in its associated knob 49. By tightening or loosening knob 49 the fossae block member 48 will either be tightened or loosened with respect to the upper support member 12, thus allowing axial positioning/spacing of the fossae block members 48 to the desired distance to match the anatomical conditions of the patient for which the articulator is being used. Such anatomical measurement, may for example, be obtained through the use of tomography as is well known in the art. Axial Tome Corporation produces and sells a suitable device for obtaining the desired anatomical measurements. Adjacent each knob 49 there is provided a lineal scale 53 so that the axial spacing of fossae block members 48 may be easily and conveniently determined by appropriate readings therefrom. In addition, an angular scale 54 is provided for setting the angle orientation of a fossae block member 48 as desired. Angular scale 54 comprises a plate 55 having a opening 56 designed to receive the shaft 50. Shaft 50 is designed to receive plate 55 such that it represents the angular position of fossae block member 48. A second plate 57 is provided which has a pair of downwardly extending projections 58 which engage a corresponding groove 59 in upper support member 12. The plates 55,57 each have respective angular markings so that the angular position of fossae block member 48 can be accurately positioned to correspond to the anatomical condition of the patient.

Each fossae block member 48 and its associated condyle 19 cooperate so as to provide a polycentric hinge joint which simulates the temporomandibular condylar joint of an individual. Preferably, the fossae block member 48 are made of an appropriate high molecular plastic material to simulate the movement in a human jaw. Examples of suitable plastic materials are polyethylene and polypropylene, however, any suitable material may be used.

Figure 4:
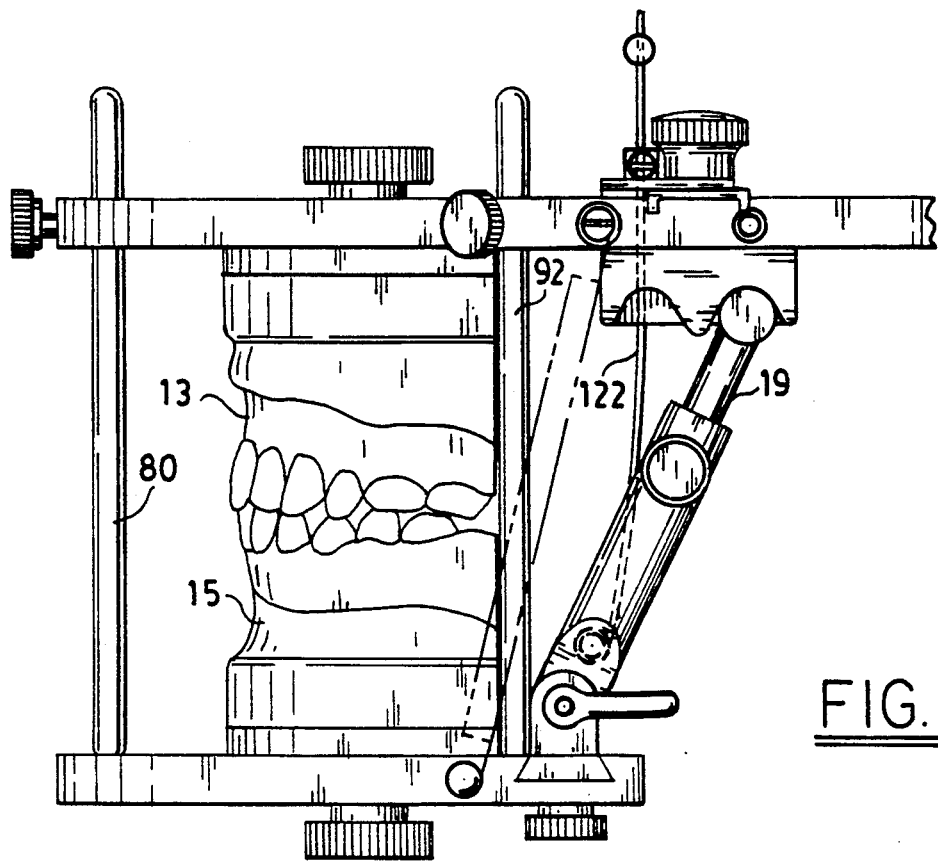
FIG. 4 is a partial view of the articulator of FIG. 1 illustrating a dental cast mounted to the upper and lower support members.

A pair of coil springs 62 is provided for securing upper support member 12 to lower support member 14 and for simulating the muscles used for mastication between the upper and lower teeth of an individual. In the embodiment illustrated a cylindrical protective plastic sheath 63 surrounded each coil spring 62. The coil springs 62 each have an upper end 64 which is secured to upper support member 12 and a lower end 65 designed to be secured to lower support member 14. In the particular embodiment illustrated, the upper end 64 is secured to upper support member 16 by a threaded member 66 which clampingly secures the upper end 64 of coil spring 62 to upper supporting member 12. It is to be understood that the upper end 64 of the coil springs 62 may be secured in any desired fashion to upper support member 12. In the particular embodiment, the lower end 65 of each spring 62 is provided with a circular loop 69 designed to receive a pin 70 secured to base member 16. The pin 70 allows lower end 65 of spring to be easily mounted and removed therefrom and also allows it to freely rotate as lower support member 14 is moved, as is discussed later herein. The coil springs 62 bias the lower support member 14 toward the support member 12. Additionally, by properly locating the position at which the upper and lower ends 64,65 are secured to upper support and lower support members 12,14, respectively, the lower support member 14 is also biased toward the rear lateral section of articulator 10 as illustrated by arrow 72 in FIG. 1. The coil springs 62 are designed to provide a sufficient amount of force such that any dental cast or orthodontic model that is placed on lower support member 14 will be adequately supported yet be of sufficient resiliency so that the position of the lower support member 14 may be easily manipulated by the user. In the particular embodiment illustrated each coil spring 62 is made of a stainless steel wire having a diameter of 0.030 inches (0.762 mm) and has an outside cross sectional diameter of 0.210 inches (5.33 mm) providing an initial loading of about 3 lbs. when the articulator is in the closed position as illustrated in FIG. 4. Spring 62 also has a spring constant of about 3¼ lbs./inches. It is of course understood that each spring 62 may be designed to provide the desired physical character desired.

Articulator 10 is also provided with means for positioning the lower support member 14 at a desired distance H with respect to said upper support member 12. This is accomplished by providing a forward removable adjustment rod 80 which passes through an opening 82 in upper support member 12. The lower end 83 of rod 80 is designed to engage the top surface 84 of base member 16. Preferably as illustrated, a recess 85 is formed in base member 16 so as to properly locate and position the lower support member 14 with respect to the upper support member 12. Locking means 86 is provided for moving rod 80 to the desired position and locking rod 82 at such desired position. In the particular embodiment illustrated, locking means 86 comprises a knob 87 having threaded shaft 88 designed to engage a threaded opening 89 which communicate with opening 82. Opening 89 allows threaded shaft 88 to pass therethrough until it engages rod 80. By appropriately tightening or loosening knob 87, rod 80 can be easily adjusted to provide the desired vertical distance H between upper support member 12 and lower support member 14. In a similar manner, a pair of axially spaced rear lateral adjustment rods 92 are also provided. The rear lateral adjustment rods 92 each extend through a respective opening 94 in the rear lateral section of upper support member 12. Locking means 96 are provided for adjusting the vertical position of rear lateral adjustment rods 92 in the same manner as locking means 86 was used to lock forward rod 80, like numerals representing like parts. Lower end 98 of rear lateral adjustment rods 92 are designed to engage and mate with the base member 16 of lower support member 14. As with forward rod 80 rear lateral adjustment rods 92 are preferably designed to mate in a dished recess 80 formed in base member 16. While adjustment rods 80 and 92 may all be used at the same time generally the adjustment rod 80 is initially used to set up the dental cast to be mounted to the articulator 10. Once the dental cast have been mounted, the rear lateral adjustment rods 92 are positioned at the pre-positioned height, forward adjustment rod 80 may be removed. This allows the user to have free access to the prosthetic devices. Preferably, as illustrated, the upper end 94 of rods 80,92 is provided with an appropriate scale 95 such that the vertical displacement between the lower support member 14 and upper support member 12 can be accurately maintained or redefined at some later time should the need arise.

As is customary with articulators of prior art, articulator 10 is appropriately provided with means for securing dental cast thereto. Thus the upper support member 12 and lower support member 14 are each provided with a mounting knob 100 having a threaded shaft 102 designed to pass through opening 103, 104 in upper and lower members 12,14, respectively and engage a mounting plate 106 upon which the appropriate dental cast or orthodontic model may be secured. Typically, as illustrated in FIG. 4, casts of the upper and lower teeth of a patient are mounted to upper support member 12 and lower support member 14, respectively. It is to be understood and appreciated that the means for securing the dental cast or orthodontic models may be varied as desired.

The upper support member 12 is secured to neck portion 110 which is in turn secured to a base 112 which allows the articulators to be placed on the desired work surface. In the embodiment illustrated upper support member 12 is secured to neck portion 110 by a knob 113 having a threaded shaft 115 which passes through an opening in upper support member 12 and engages a threaded opening in neck portion 110. However, upper support member 12 may be secured to neck portion 110 in any desired manner. The base 112 is provided with a plurality of feet 114 such that the base 112 is spaced slightly from the table or bench upon which the articulator 10 is placed. It is to be understood that the configuration of base 112 and the number and design of feet 114 may be varied as desired. Preferably as illustrated the neck portion 110 is releasably secured to base 92 such that the neck portion 110 may be used to lift the upper and lower members 12,14 with their appropriate dental cast devices thereon and manipulated by the user as desired. This allows the user to view the dental cast at any appropriate angle. The neck portion 110 in the particular embodiment illustrated is releasably mounted to base 92 through the use of a threaded knob 116 having a threaded shaft 118 which engages a threaded opening 120 in the bottom of neck portion 110. It is to be understood that the neck portion 110 may be releasably mounted to the base in any desired manner, the illustrated embodiment being only one means by which this may be accomplished.

The articulator is also provided with means for simulating the ligament of a jaw, in particular, the stylo-mandibular and spheno-mandibular ligaments in the mouth. This is accomplished through the use of a pair of wires 122 which pass through an opening 124 in the upper support member 12. Each of these wires 122 are designed to simulate the ligaments on either side of the patient's jaw. In the particular embodiment illustrated each wire 122 is made of a spring type metal. The lower end 126 of wire 122 is secured to the lower end of central support section 20. The opening 124 is sized so as to allow the wire 122 to freely move therethrough. At the upper end 127 of each wire 122 above upper support member 12 there is provided a locking means 128 designed to restrict the amount of movement of the wire 122. In the particular embodiment illustrated means 128 comprises a block 130 having an opening 131 designed to allow the upper end of wires 127 to freely pass therethrough. A screw 132 is provided which passes through an appropriate threaded opening 134 in each block 130 such that the screw 132 engages the wire 122. The screw 132 is designed such that when tightened against wire 122, the screw 132 will permanently position the block 130 at any desired location. By determining the position of block 130 with respect to the upper surface 135 of upper support member 12, this will restrict the overall movement of the lower support member 14 with respect to the upper support member 12. If the lower support member 14 is moved too far, the block member 130 will engage the upper surface 135 of upper support member 12 thus restricting any further movement along an arc which is determined by the length of the wire 122 between the block 130 and condyle. By taking appropriate measurements from the patient, the amount of movement can be restricted as desired by the user.

Figure 5:
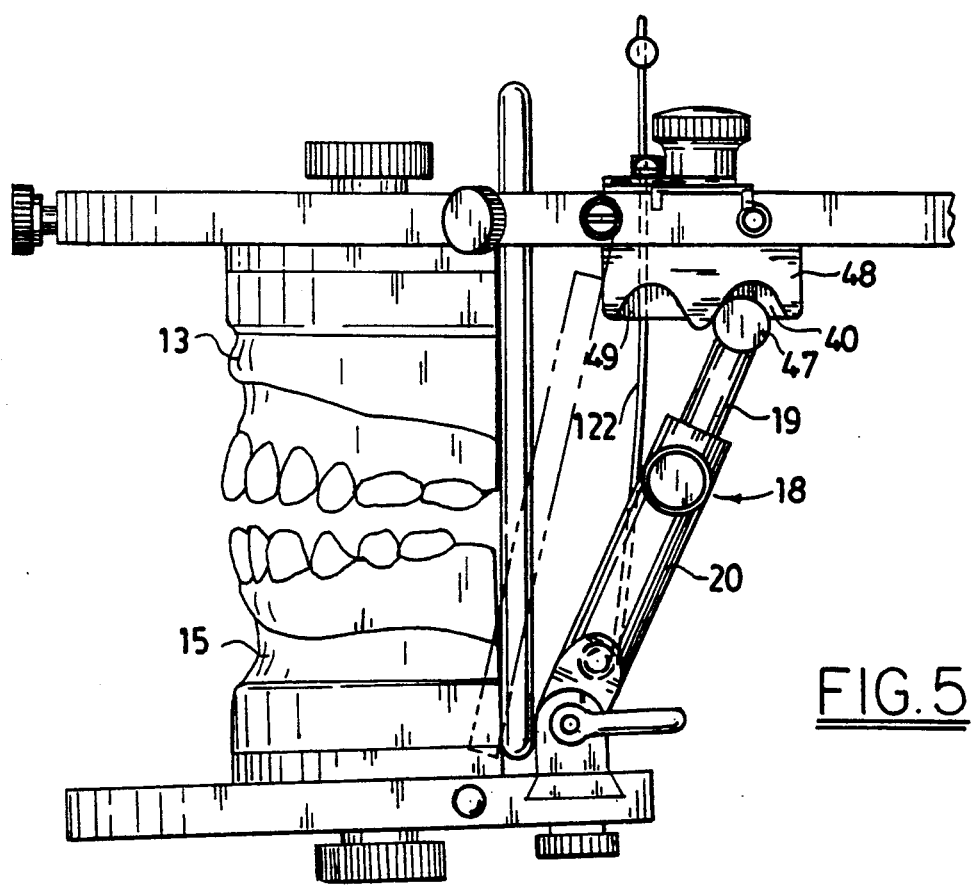
FIG. 5 is a view similar to FIG. 4 illustrating the articulator in a first partially open position.
Figure 6:
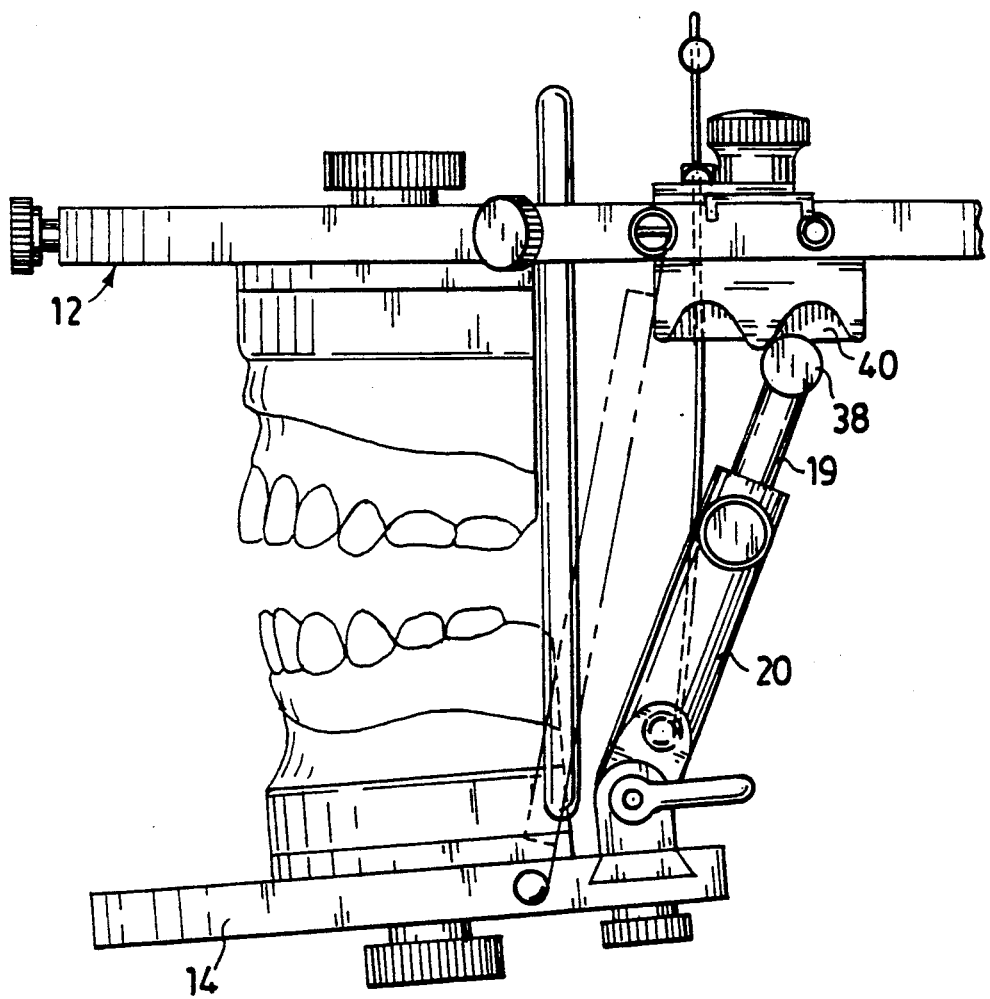
FIG. 6 is a view similar to FIG. 4 illustrating the lower support member being moved in a second fully opened position.
Figure 7:
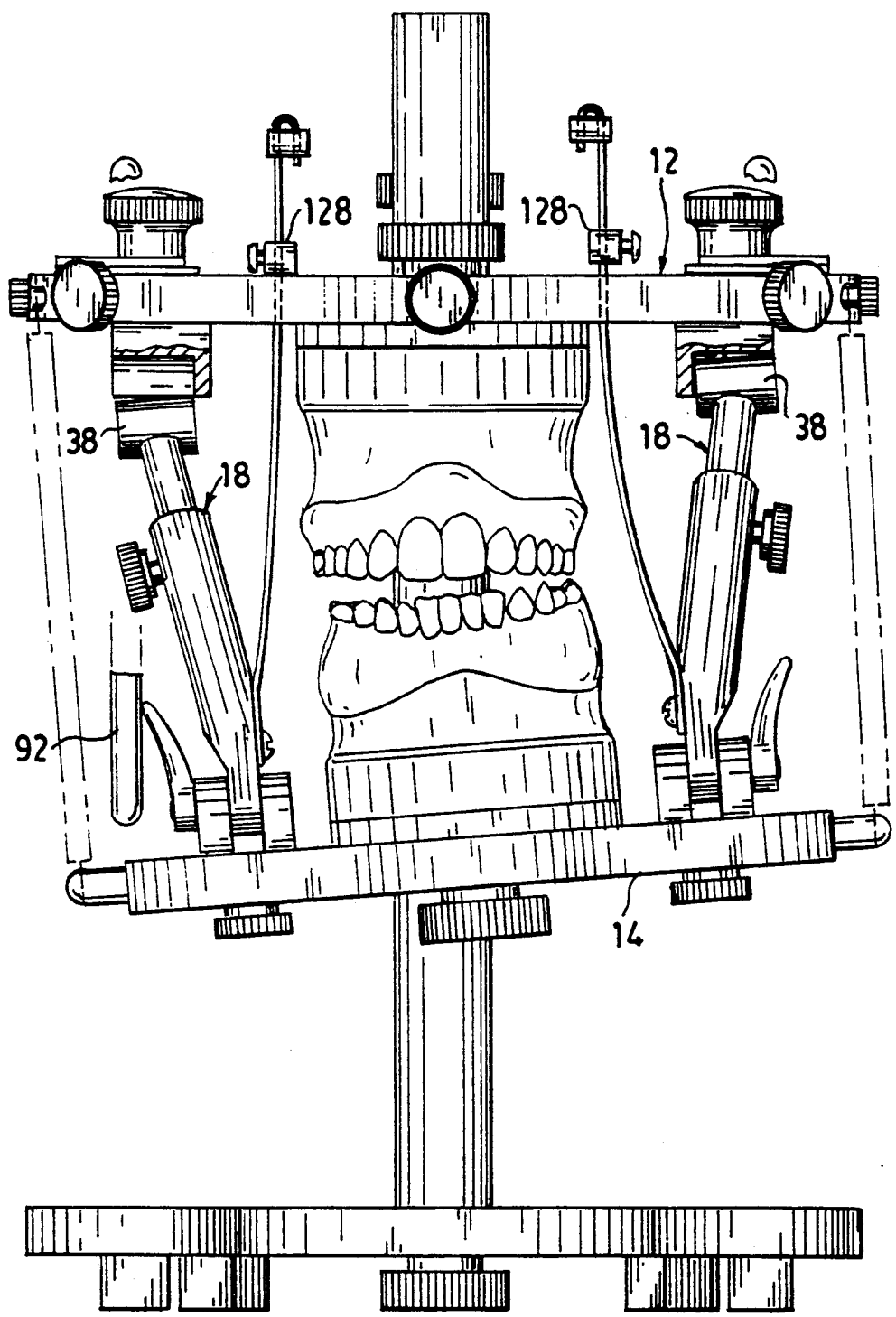
FIG. 7 is a front elevational view similar to FIG. 2 illustrating dental cast mounted thereon and the articulator moved to simulate lateral movement of the jaw.
Figure 8A:
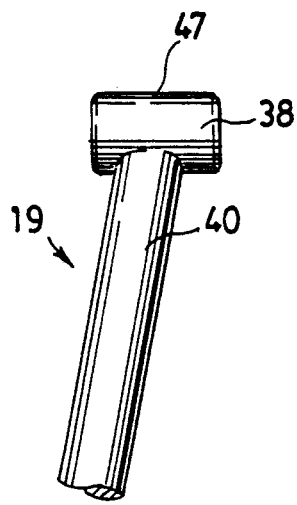
FIG. 8A is a front elevational of a condyle member used in the articulator in the present invention.
Figure 8B:
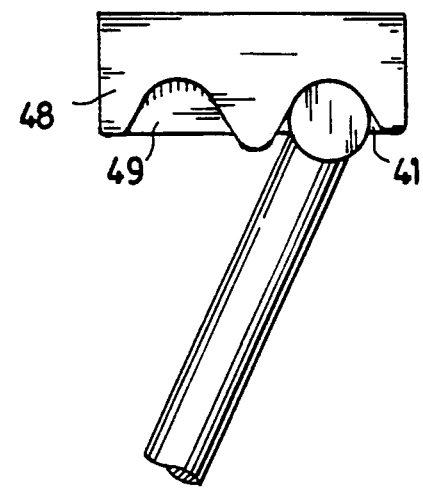
FIG. 8B is a side elevational view of a condyle of FIG. 8 as placed in its respective fossae block member when the articulator is in the closed position as illustrated in FIG. 4.
Figure 8C:
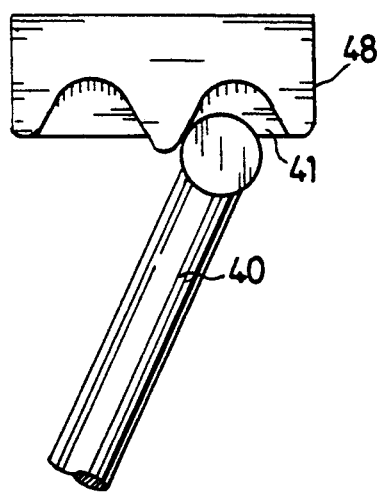
FIG. 8C is a partial view of a condyle of FIG. 8B illustrating the condyle wherein the articulator is in the first partially opened position as illustrated in FIG. 5.
Figure 8D:
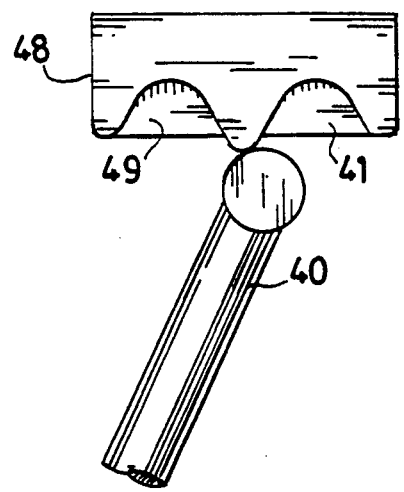
FIG. 8D is an enlarged sectional view of a condyle of FIG. 8B wherein the articulator is in the second fully opened position as illustrated by FIG. 6.
Figure 9A:
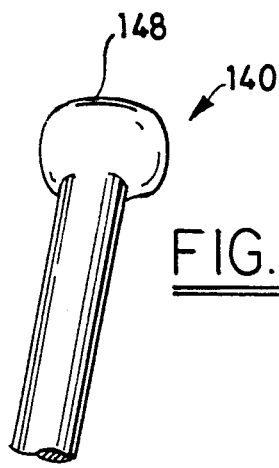
FIG. 9A is a front elevational of a modified condyle mode in accordance with the present invention which has been designed to have a configuration similar to that of a patient.
Figure 9B:
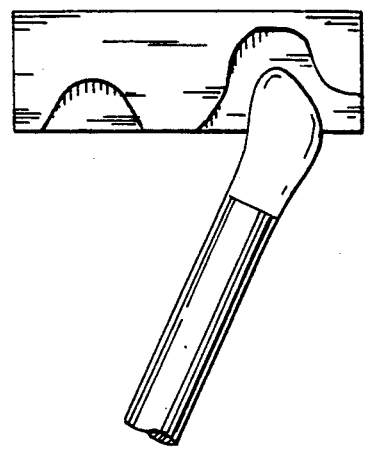
FIG. 9B is a side elevational view of the condyle of FIG. 9A as illustrated in an associated fossae block member also designed to replicate the actual configuration of temporomandibular joining of the patient.
Figure 9C:
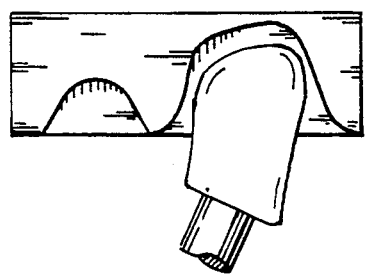
FIG. 9C-9E illustrate various other cross-sectional configurations of other condyle members and associated fossae block members designed to replicate various configuration of temporomandibular joints formed in the patients.
Figure 9D:
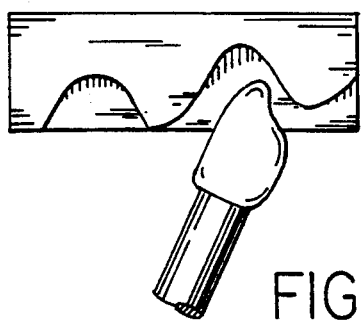
Figure 9E:
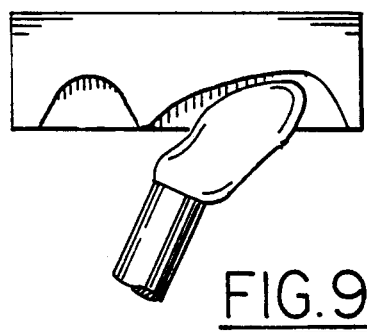
Figure 10:
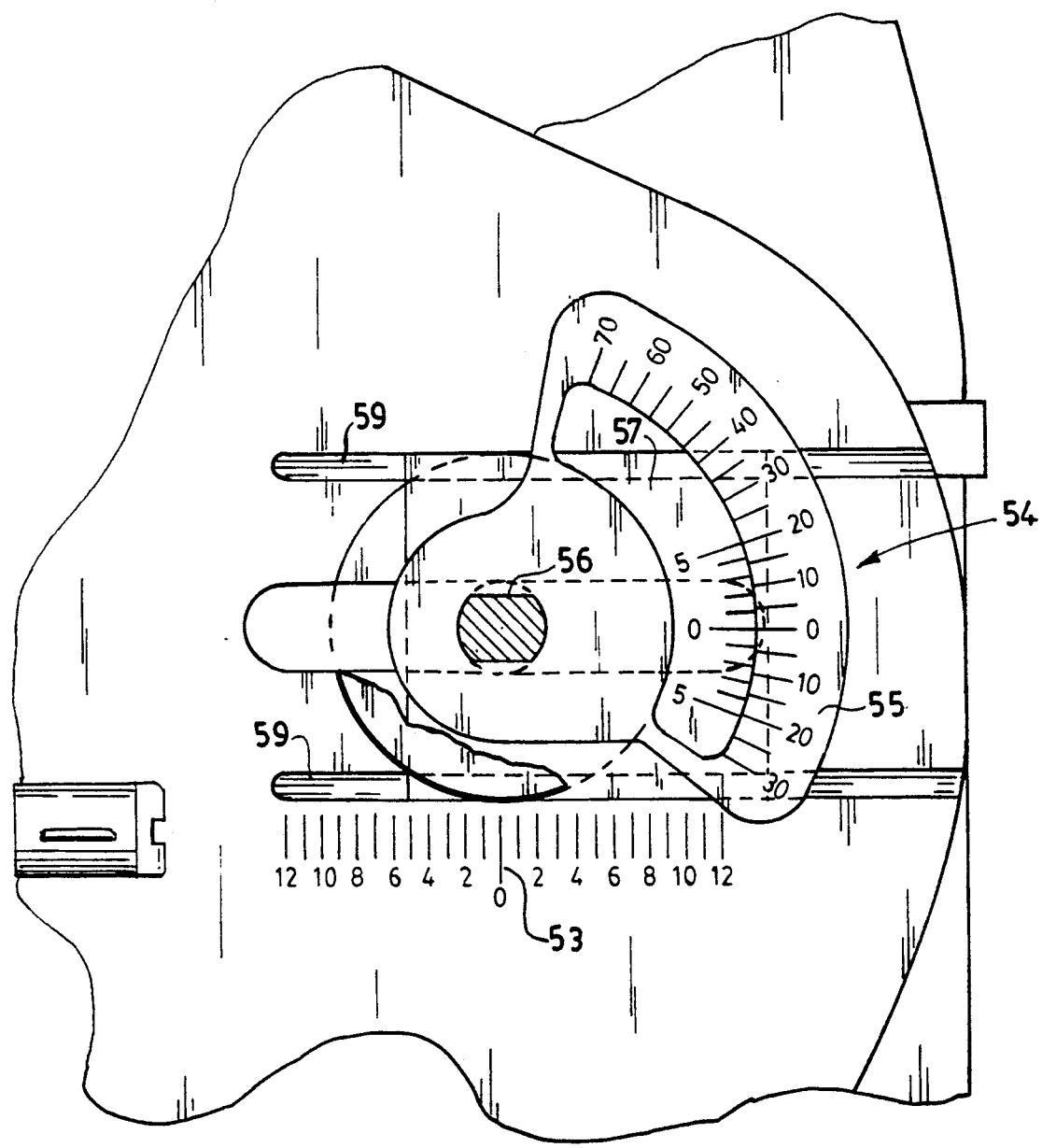
FIG. 10 is an enlarged partial top plan view of FIG. 3 illustrating the means used to secure and orientate each fossae block member to the articulator.

In order to more fully appreciate the advantages of the present invention, Applicant will now briefly describe the operation of the articulator 10. As illustrated in FIG. 4, dental prosthetic devices are mounted to the upper and lower support members 12,14. Adjustment rod 80 is moved to the desired location and secured in position so as to provide the desired vertical distance H between the upper and lower support members 12,14. Once this has been done, the rear lateral adjustment rods 92 may be placed in position and secured. Thereafter forward adjustment rod 80 may be removed entirely if so desired. The lower support member 14 may be moved freely, for example, as illustrated in FIGS. 5, 6, 7 so as to separate the lower dental cast from the upper dental cast. Since the condyle 19 is not permanently affixed to the fossae block member 48 the condyle 19 is allowed to freely move within the fossae recess. As illustrated in FIGS. 9C-9E the condyle is free to move downward and axially inward much in the same way the condyle of an actual jaw moves in a human being. As can be seen, the center C of upper engaging section 38 moves in response to movement of the lower support member 19, thus provides a polycentric hinge for the temporomandibular joint. The coil spring maintains the lower support member in relationship to the upper support member. The wires 122 resist the movement of the lower support member 14 so as to simulate the ligament of the jaw. However, the user is able to more freely move lower support member to simulate the actual movement of the lower jaw of a patient. The lower support member 14 can be moved in any direction permitted by the coil springs 62 and wires 122. Additionally, the condyle 19 moves such that outer surface 47 as it engages recess 40 simulates a human temporomandibular condylar joint. Thus, allowing the upper engaging surface 38 to ride on the area of fossae block member 48 which simulates the superior eminence. In the event engaging section 38 disengages from recess 40, it will be captured in capture recess 49 so that the user will not loose control of the device.

Referring to FIG. 8 there is illustrated how the lateral movement may occur to simulate lateral movement in a temporomandibular joint. In particular, the condyle 19 on the left-hand side (as seen by the viewer) leaves the corresponding fossae recess in fossae block member. The block member 108 is associated with wire 122 secured to the condyle support member 18 is moved that the block rests against the top surface, whereas the condyle on the right-hand side is moved only slightly. Thus it can be seen that lateral displacement of the lower support member cannot be effectuated.

Referring to FIG. 9, there is illustrated a front elevational view of a modified condyle 140 made also in accordance with the present invention. In this particular embodiment outer engagement surface 148 is substantially round as viewed in the frontal view and has a cross-sectional configuration as illustrated in FIG. 9. These shaped configurations more closely resemble actual condyle temporomandibular joints as exist in patients. By simply modifying the configuration of the condyle 19, more accurate movement of the lower jaw may be had as it closely resembles that actually occurring in the patient. FIGS. 9C, 9D and 9E illustrated various other configurations that may 1 condyle 19 and fossae recess 40. It is of course to be understood that the configuration of condyle may be varied to any shape.

It is to be understood that various other changes and modifications may be made without departing from the spirit or scope of the present invention. The present invention being defined by the attached claims.

What is claimed is:

1. A dental articulator comprising:
   an upper support member for supporting a first dental cast, orthodontic model or other dental device;
   a lower support member having a base member for supporting a second dental cast, orthodontic model or other dental device and a pair of axially spaced condyle support members extending therefrom towards said upper support member;
   polycentric hinge joint means for simulating the temporomandibular condylar joint and for mounting said lower support member to said upper support member, said polycentric hinge joint means comprising a pair of fossae block members mounted to said upper support member, each fossae block member having a fossae recess, a condyle member secured to each of said condyle support members, each of said condyle members having an outer engaging surface for mating with its corresponding fossae recess, means for simulating the muscles for mastication and for biasing said lower support member to said upper support member, and means for simulating the ligaments of a patient which secure said lower jaw to said upper jaw comprising a pair of flexible connecting elements, one of said connecting elements being associated with each of said condyle support members, each of said connecting elements having a lower end and an upper end, said lower end being secured to its associated condyle support member, said upper end being secured to said upper support member.

2. A dental articulator according to claim 1 wherein said means for simulating the muscles used for mastication and for biasing said lower support members to said upper support member comprises a pair of axially spaced coil springs each having a lower end and upper end, the lower end of each of said coil springs being secured to said lower support member and the upper end of said coil spring being mounted to said upper support member such that said lower support member is biased upward and backward with respect to said upper support member.

3. A dental articulator according to claim 2 wherein said coil springs made of stainless steel wire provides an initial loading of about 3 lbs. and has a spring constant of about 3.5 lbs./inches.

4. A dental articulator according to claim 3 wherein said coil springs are made of wire having a diameter of about 0.030 inches (0.762 mm) and has an outside diameter of about 0.210 inches (5.33 mm).

5. A dental articulator according to claim 1 wherein said upper end of each said connecting element has means for adjusting the degree of movement said lower support member may have with respect to said upper support member.

6. A dental articulator according to claim 5 wherein said means for adjusting the degree of movement comprises of a block having a hole through which said upper end of said connecting element extends and a set screw for adjusting and securing the position of said block along the upper end of said wire, said block being designed to bear against the upper surface of said upper support member.

7. A dental articulator according to claim 5 wherein said flexible connecting elements are made of a nickel titanium ally.

8. A dental articulator according to claim 7 wherein said flexible connecting element has a diameter of about 0.027 inches (0.6858 mm).

9. A dental articulator according to claim 1 wherein said condyle member is adjustably mounted to said condyle support member such that said condyle member may be easily removed and replaced.

10. A dental articulator according to claim 1 wherein each of said fossae block members is mounted to said upper support member by a hand adjustment means having a shaft extending through a slot in said upper support member, said hand adjustment means allowing for axial spacing of said fossae block members to a desired distance and for locking said fossae block members in position.

11. A dental articulator according to claim 10 wherein each of said fossae block members may be adjusted to orient said block members at a desired angle with respect to the dental cast placed in said articulator.

12. A dental articulator comprising:
an upper support member for supporting a first dental cast;
a lower support member having a base member for supporting a second dental cast;
joint means for simulating the mandibular condylar joint and for mounting said lower support member to said upper support member;
means for simulating the ligaments of a patient connecting said upper support member to said lower support member, said means for simulating the ligaments of a patient comprises a pair of flexible connecting elements, one of said flexible connecting elements being associated with each of said condyle support members, each of said connecting elements having a lower end and an upper end, said lower end being secured to its associated condyle support member, said upper end being secured to said upper support member.

13. A dental articulator according to claim 12 wherein said upper end of each said connecting element has means for adjusting the degree of movement said lower support member may have with respect to said upper support member.

14. A dental articulator according to claim 13 wherein said means for adjusting the degree of movement comprises a block having a hole through which said upper end of said connecting element extends and a set screw for adjusting and securing the position of said block along the upper end of said connecting element, said block being designed to bear against the upper surface of said upper support member.

15. A dental articulator according to claim 13 wherein said flexible connecting elements are made of a nickel titanium alloy.

16. A dental articulator according to claim 15 wherein said flexible connecting element has a diameter of about 0.027 inches (0.6858 mm).

17. A dental articulator according to claim 12 further comprising:
means for positioning said lower support member with respect to said upper support member a desired distance comprising, a first removable adjustment rod, said first removable adjustment rod passing through a hole in said upper support member which is located at the forward end of said upper support member and allows the lower end of said adjustable rod to bear against the upper surface of said lower support member, means for locking said first removable rear adjustment rod at a desired position, at least one removable rear adjustment rod located at the rear end of said articulator, said at least one rear adjustment rod passing through an opening in the rear end of said upper support member allowing the lower end of said at least one removable rear adjustment rod to bear against the upper surface of said lower support member and allow said first removable adjustment rod to be removed from said articulator means for locking in position said at least one removable rear adjustment rod in said rear end of said upper support member at a desired position.

18. A dental articulator according to claim 17 wherein said at least one rear adjustment rod located at the rear end of said upper support member comprises two axially spaced rear lateral adjustment rods, said two rear adjustment rods having means for monitoring and controlling the distance at which said upper support and lower support member are positioned.

19. A dental articulator according to claim 18 wherein said lower support member is provided with recess dished sections for receiving said first removable adjustment rod and at least one removable adjustment rod.

20. A dental articulator according to claim 17 wherein said first removable adjustment rod and at least one removable rear adjustment rod each has scale means for monitoring the distance between said upper support member and lower support member.

21. A dental articulator according to claim 17 wherein said means for locking in position said first adjustment rod and said at least one removable rear adjustment rod comprises a knob having a threaded shaft which engages a threaded opening in said upper support member which communicates with said openings, said first removable adjustment rod and at least one removable rear adjustment rod passing through so that said threaded shaft can bear against said rods to hold them firmly in place.

22. A dental articulator according to claim 12 further comprising:
- a neck portion secured at the rearward end of said upper support member;
- a base portion secured to the lower end of said neck portion, said neck portion having a length such that said lower support member is spaced rom said base support member.

23. A dental articulator according to claim 22 further comprising means for allowing the neck portion to be readily disconnected from said base section so that said neck portion, said upper support member and said lower support member can be easily manipulated by the user.

24. A dental articulator according to claim 23 wherein said means for allowing the neck to be removed from said base portion comprises a knob having a threaded shaft secured thereto, said threaded shaft passing through an opening in said base portion and engages a threaded opening in the bottom of said neck portion.

25. A dental articulator according to claim 22 wherein the upper support member is secured to the top of said neck portion by a knob having a threaded shaft secured thereto which passes through an opening in upper support member to engage a threaded opening in neck portion so as to secure said upper support member to said neck portion.

26. A dental articulator according to claim 22 wherein said upper support member is secured to said neck portion so that said upper support member and lower support member may be invertedly secured to said neck portion.

27. A dental articulator comprising:
- an upper support member for supporting a first dental cast, orthodontic model or other dental device;
- a lower support member having a base member for supporting a second dental cast, orthodontic model or other dental device and a pair of axially spaced condyle support members extending therefrom towards said upper support member, said condyle support members having adjustable locking hinge means for positioning and locking said condyle support members at a desired angle with respect to said base member;
- polycentric hinge joint means for simulating the temporomandibular condylar joint and for mounting said lower support member to said upper support member, said polycentric hinge joint means comprising a pair of fossae block members mounted to said upper support member, each fossae block member having a fossae recess, a condyle member secured to each of said condyle support members, each of said condyle members having an outer engaging surface for mating with its corresponding fossae recess, and means for simulating the muscles for mastication and for biasing said lower support member to said upper support member.

* * * * *

UNITED STATES PATENT AND TRADEMARK OFFICE
CERTIFICATE OF CORRECTION

PATENT NO. : 5,160,262
DATED : November 3, 1992
INVENTOR(S) : Michael C. Alpern et al.

It is certified that error appears in the above-identified patent and that said Letters Patent is hereby corrected as shown below:

Column 2, line 52, please insert --view-- after "elevational" and before "of".

Column 9, line 30, "ally" should be --alloy--.

Column 11, line 9, "rom" should be --from--.

Signed and Sealed this

Eighth Day of February, 1994

Attest:

BRUCE LEHMAN

*Attesting Officer*      *Commissioner of Patents and Trademarks*